US012797144B2

(12) United States Patent
Shindo

(10) Patent No.: US 12,797,144 B2
(45) Date of Patent: Nov. 17, 2026

(54) SURGICAL INSTRUMENT

(71) Applicant: RIVERFIELD INC., Tokyo (JP)

(72) Inventor: Koki Shindo, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 42 days.

(21) Appl. No.: 18/750,884

(22) Filed: Jun. 21, 2024

(65) Prior Publication Data

US 2024/0350210 A1 Oct. 24, 2024

Related U.S. Application Data

(63) Continuation of application No. PCT/JP2022/001630, filed on Jan. 18, 2022.

(51) Int. Cl.
*A61B 34/30* (2016.01)

(52) U.S. Cl.
CPC .................................... *A61B 34/30* (2016.02)

(58) Field of Classification Search
CPC ......... A61B 34/30; A61B 34/37; A61B 34/71; A61B 2018/00178; A61B 34/70; A61B 34/76; A61B 17/2909; A61B 17/00296; A61B 17/2804; A61B 2017/00367; A61B 2017/2924; A61B 2017/0046; A61B 2017/00477; A61B 2017/00323; A61B 2034/718; A61B 2034/301; A61B 2034/302; A61B 1/00; A61B 1/00064; B25J 9/0009; B25J 17/00
See application file for complete search history.

(56) References Cited

U.S. PATENT DOCUMENTS

| | | | | |
|---|---|---|---|---|
| 2005/0240178 A1* | 10/2005 | Morley | A61B 18/1445 606/51 |
| 2006/0079889 A1* | 4/2006 | Scott | A61B 18/1445 606/45 |
| 2011/0313405 A1 | 12/2011 | Anderson et al. | |
| 2014/0350540 A1* | 11/2014 | Kitagawa | A61B 18/1445 606/34 |
| 2018/0228562 A1* | 8/2018 | Robert | A61B 17/00234 |
| 2018/0325579 A1 | 11/2018 | Haughton et al. | |
| 2020/0000512 A1* | 1/2020 | Heiliger | A61B 18/1445 |
| 2022/0211402 A1* | 7/2022 | Shindo | A61B 1/00 |

FOREIGN PATENT DOCUMENTS

| | | | |
|---|---|---|---|
| JP | 6747745 B1 | 8/2020 | |
| WO | WO-2021140623 A1 * | 7/2021 | A61B 1/00064 |

* cited by examiner

*Primary Examiner* — Shaun L David
*Assistant Examiner* — Cherie M Poland
(74) *Attorney, Agent, or Firm* — Sughrue Mion, PLLC

(57) ABSTRACT

A surgical instrument includes a casing including a first end and a second end, the second end being opposite from the first end, a moveable part attached to a shaft extending from the first end of the casing, at least one slider movable with respect to a casing, at least one wire being held by the at least one slider, the at least one wire being configured to transmit movement from the at least one slider to the movable part, a conductor arranged in the casing and configured to conduct an electric power to the movable part, and an insulator that covers an end portion of the at least one wire that extends from the at least one slider toward the second end of the casing. The insulator may include a covering area covering the end portion of the at least one wire, and a non-covering area.

20 Claims, 10 Drawing Sheets

SURGICAL INSTRUMENT

CROSS-REFERENCE TO RELATED APPLICATIONS

This Application is a continuation of International Application No. PCT/JP2022/001630, filed on Jan. 18, 2022 in the Japan Patent Office, the contents of which being incorporated by reference herein in its entirety.

BACKGROUND

The present disclosure relates to a surgical instrument.

Regarding master-slave surgical robots, various methods for driving a surgical instrument mounted on such surgical robot have been used.

SUMMARY

According to an aspect of one or more embodiments, there is provided a surgical instrument including a casing including a first end and a second end, the second end being opposite from the first end, a moveable part attached to a shaft extending from the first end of the casing, at least one slider movable with respect to a casing, at least one wire being held by the at least one slider, the at least one wire being configured to transmit movement from the at least one slider to the movable part, a conductor arranged in the casing and configured to conduct an electric power to the movable part, and an insulator that covers an end portion of the at least one wire that extends from the at least one slider toward the second end of the casing. The insulator may include a covering area covering the end portion of the at least one wire, and a non-covering area.

According to another aspect of one or embodiments, there is provided a surgical instrument including a casing including a first end and a second end, the second end being opposite from the first end, a joint and a forceps attached to a shaft extending from the first end of the casing, a plurality of sliders being linearly movable with respect to the casing, a plurality of wires held by the plurality of sliders, an end portion of each of the plurality of wires extending from the plurality of sliders toward the second end of the casing, the plurality of wires being configured to transmit a driving force from the plurality of sliders to the joint and the forceps, a conductor arranged in the casing and configured to conduct high-frequency current to the joint and the forceps, and an insulator covering an end portion of the plurality of wires that extends from the plurality of sliders toward the second end of the casing. The insulator may include a covering area covering the end portions of the plurality of wires, and a non-covering area having a length based on the high frequency current.

DETAILED DESCRIPTION

Figure 1:
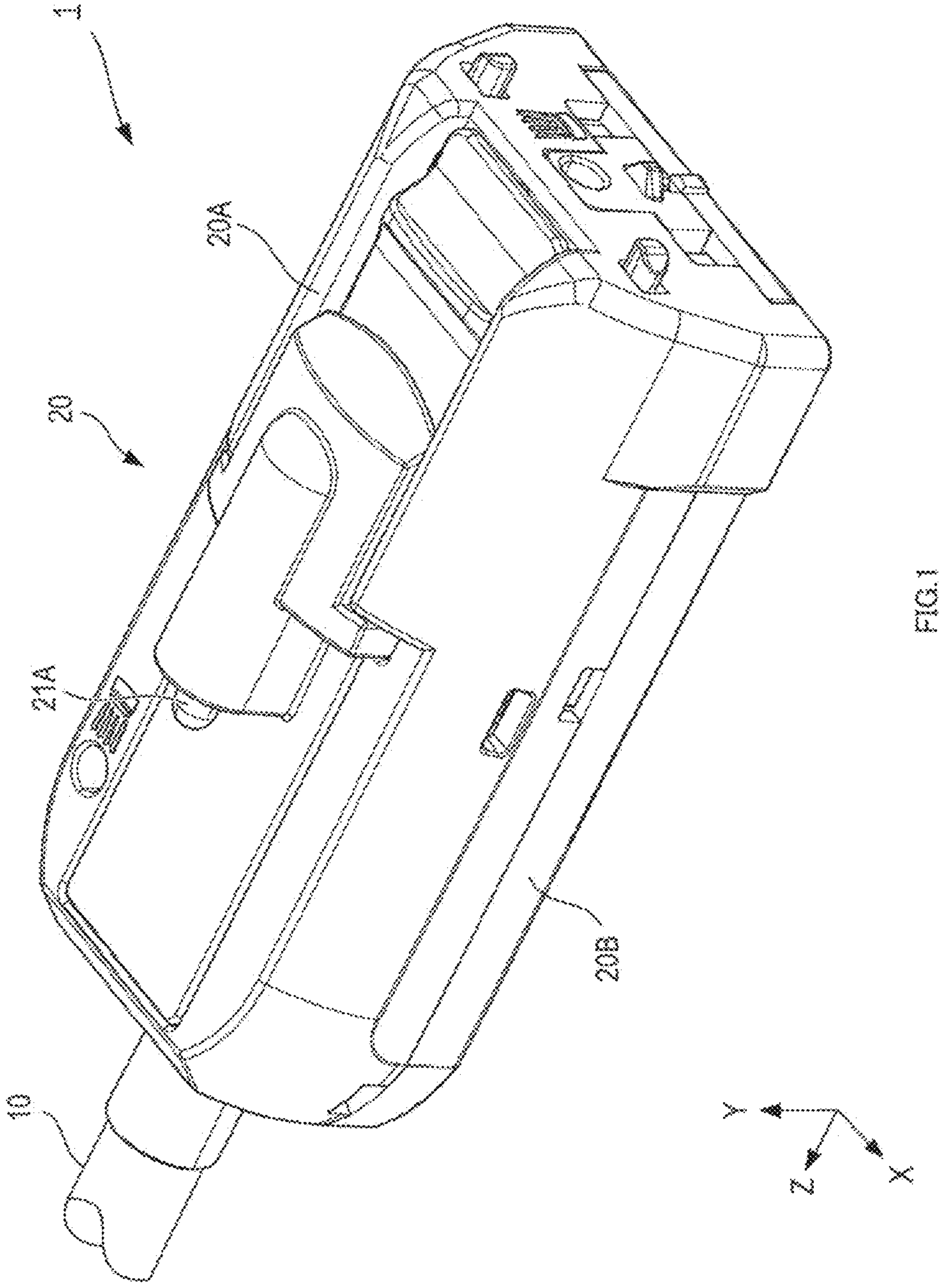
FIG. 1 is a perspective view of a surgical instrument according to some embodiments.

As discussed above, in master-slave surgical robots, various methods for driving a surgical instrument mounted on such surgical robot have been used. For example, a driving force from an actuator may be generated and the driving force may be transmitted through a slider or a wire to the surgical instrument.

Another example may include an electric scalpel, forceps, and the like as the surgical instrument mounted on the surgical robot that use high-frequency current to drive the electric scalpel, forceps, and the like. In such surgical instrument using high-frequency current, a conductor that supplies the high-frequency current to the forceps and the like is provided inside the surgical instrument. Meanwhile, the wires used to transmit the driving force may be made of metallic materials such as stainless steel so as to satisfy conditions such as strength and flexibility.

In a case that the wires used to transmit the driving force are made of conductive metallic materials, the wires need to be insulated to inhibit the high-frequency current from flowing to other portions of the surgical instrument other than an intended objective portion (e.g., the forceps at the distal end of the surgical instrument). As such, a distance needs to be set to ensure proper insulation between the wires used to transmit the driving force and the conductor of the high-frequency current. Such a distance is hereinafter also referred to as a “spatial distance”.

The wires used to transmit the driving force may be housed in a cartridge and relatively movable with respect to the cartridge. In such cases, it is advantageous to make a distance between a position of the wires that is closest to the conductor within their moving ranges and a position of the conductor wider than the spatial distance.

By doing so, the cartridge of the surgical instrument, in which the wires used to transmit the driving force and the conductor of the high-frequency current are housed, becomes larger. When the cartridge becomes larger and a plurality of surgical instruments are mounted on the surgical robot, distances between each position of the surgical instruments also become wider.

When using the surgical robot equipped with such surgical instruments to perform surgery such as robotic endoscopic surgery, it is advantageous to widen distances between a plurality of ports. A port is a member to be placed at a site of surgery and is a tubular member into which a shaft of the surgical instrument is inserted.

If the distances between the plurality of ports are wider, various limitations tend to occur in an attempt to approach an objective tissue to be operated by using the surgical instruments mounted on the surgical robot. As such, it becomes increasingly difficult to perform clinical cases using the surgical robot.

It is an aspect to provide a surgical instrument having proper insulation between end portions of wires used to transmit the driving force and a conductor of the high-frequency current without increasing a distance therebetween, and to reduce a size of a casing in which the wires, the conductor, and the like are housed. Accordingly, when surgical instruments are mounted on the surgical robot, the distances between the wires are inhibited from being widened.

According to some embodiments, a surgical instrument including a casing including a first end and a second end, the second end being opposite from the first end, a moveable part attached to a shaft extending from the first end of the casing, at least one slider movable with respect to a casing, at least one wire being held by the at least one slider, the at least one wire being configured to transmit movement from the at least one slider to the movable part, a conductor arranged in the casing and configured to conduct an electric power to the movable part, and an insulator that covers an end portion of the at least one wire that extends from the at least one slider toward the second end of the casing. The insulator may include a covering area covering the end portion of the at least one wire, and a non-covering area.

The at least one slider may be linearly movable with respect to the casing.

According to this configuration, the end portions of the wires extending to a side other than that of the movable part are covered by the insulator. The insulator includes the non-covering area with none of the wires arranged inside the insulator, thus making it easier to maintain the insulation even without increasing a distance between the end portions of the wires and the conductor. In other words, this configuration makes it easier to reduce a size of the casing in which the wires and the conductor are housed.

According to some embodiments, the non-covering area of the insulator may have a length greater than or equal to a spatial distance. The special distance may be based on the electric power to be supplied to the conductor.

According to this configuration, the non-covering area has the specified length. The specified length is greater than or equal to a spatial distance that is determined based on the electric power to be supplied to the conductor, so that it is easier to maintain the insulation between the end portions of the wires and the conductor.

According to some embodiments, the at least one wire may include a plurality of wires. The insulator may cover the end portions of the plurality of wires.

According to this configuration, the end portions of the plurality of wires are brought together and covered by the insulator. By covering the plurality of end portions of the plurality of wires together with the insulator, it is easier to maintain the insulation between such end portions and the conductor.

According to some embodiments, the at least one wire may be made of at least one of stainless steel, tungsten, an alloy containing tungsten, or a piano wire.

According to some embodiments, the insulator may be tubular.

According to some embodiments, the covering area and the non-covering area may be continuously arranged in a longitudinal direction of the insulator.

According to some embodiments, the covering area may be an area where the at least one wire is arranged inside the insulator in an inner part of a coaxial-section intersecting a longitudinal direction of the insulator.

According to some embodiments, the non-covering area may be an area where the at least one wire is not arranged inside the insulator.

According to some embodiments, the length of the non-covering area of the insulator may be 3 mm to 80 mm.

According to some embodiments, the length of the non-covering area of the insulator may be 3 mm to 40 mm.

According to some embodiments, the movable part may be a joint and a forceps.

According to some embodiments, the at least one wire may be configured to move the joint to change an orientation of the forceps based on a movement of the at least one slider.

According to some embodiments, the casing may include a first casing and a second casing, and the first casing may include the conductor.

According to some embodiments, the first casing may form a plurality of side faces and a top face of the casing. The conductor may be arranged on the top face of the casing.

According to some embodiments, the second casing may form a bottom face of the casing. The second casing may include the at least one slider and the at least one wire, the at least one slider being arranged in at least one groove on the second casing.

According to some embodiments, the conductor may be made of copper or an alloy containing copper.

According to some embodiments, the at least one slider may include a plurality of sliders. The at least one wire may include a plurality of wires, and each slider may be provided with one or two wires of the plurality of wires.

It is another aspect to provide a surgical instrument including a casing including a first end and a second end, the second end being opposite from the first end, a joint and a forceps attached to a shaft extending from the first end of the casing, a plurality of sliders being linearly movable with respect to the casing, a plurality of wires held by the plurality of sliders, an end portion of each of the plurality of wires extending from the plurality of sliders toward the second end of the casing, the plurality of wires being configured to transmit a driving force from the plurality of sliders to the joint and the forceps, a conductor arranged in the casing and configured to conduct high-frequency current to the joint and the forceps, and an insulator covering an end portion of the plurality of wires that extends from the plurality of sliders toward the second end of the casing. The insulator may include a covering area covering the end portions of the plurality of wires, and a non-covering area having a length based on the high frequency current.

According to some embodiments, the length of the non-covering area of the insulator may be greater than or equal to a spatial distance based on the electric power to be supplied to the conductor.

According to some embodiments, the end portion of the plurality of wires may include a plurality of end portions and the insulator may cover a circumference of the plurality of end portions of the plurality of wires.

Various embodiments will now be described with reference to the drawings. Components, members, and processes that are the same as or equivalent to each other illustrated in the drawings are represented by the same reference numerals, and redundant explanation will not be repeated where appropriate for conciseness. The present disclosure is not to limited by the various embodiments described herein, but rather the various embodiments are provided as examples, and any feature or any combination of features described in the various embodiments is not necessarily essential. As used in this specification, the phrase “at least one of A, B, or C” includes within its scope “only A”, “only B”, “only C”, “A and B”, “B and C”, “A and C”, and “A, B and C”.

A surgical instrument according to some embodiments is described with reference to FIGS. 1 through 7. A surgical instrument 1 according to some embodiments may be an instrument provided on a multi-degree-of-freedom manipulator in a surgical robot that is remotely controllable. The surgical instrument 1 may have a configuration of a forceps or the like for use in treating a patient during endoscopic surgery, for example.

Figure 2:
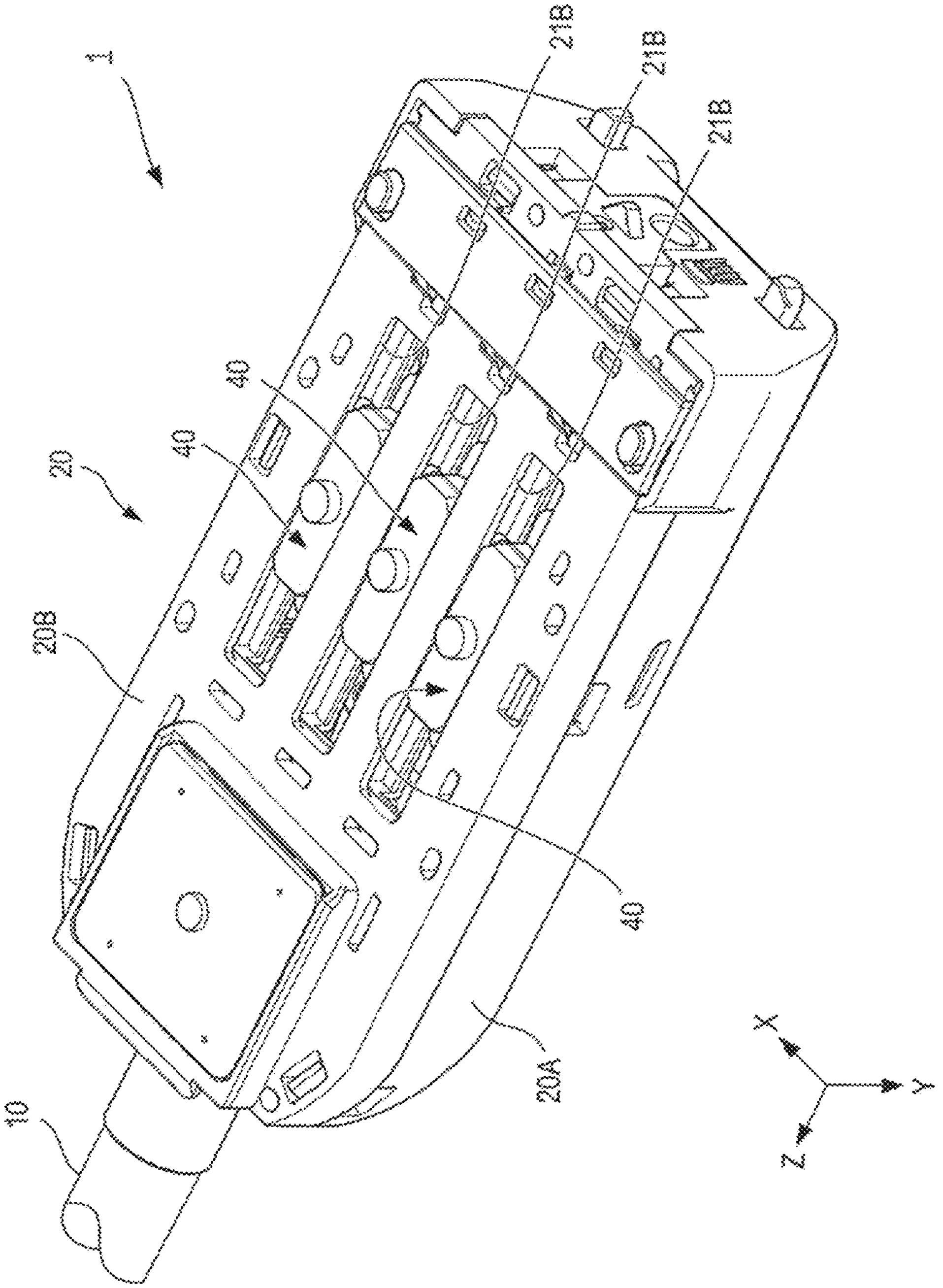
FIG. 2 is a perspective view of the surgical instrument according to some embodiments.

As shown in FIGS. 1 and 2, the surgical instrument 1 may include a shaft 10 and a casing 20.

To simplify the description of some embodiments, a direction in which the shaft 10 extends is described as a Z-axis, and a direction toward a leading end from a base of the shaft 10 is described as a positive direction of the Z-axis. In addition, a direction which is orthogonal to the Z-axis and along which later-described two or more sliders 40 are aligned is described as an X-axis, and a left direction when facing in the positive direction of the Z-axis is described as a positive direction of the X-axis. Further, a direction orthogonal to the Z-axis and to the X-axis is described as a Y-axis, and a direction from the surface where the sliders 40 are aligned in the casing 20 to an opposite surface is described as a positive direction of the Y-axis.

The shaft 10 may be a rod-shaped member to be inserted into a body of a patient. The shaft 10 may be disposed to extend from the casing 20 in the positive direction of the Z-axis. The shaft 10 may be configured to have a columnar or a cylindrical shape.

According to some embodiments, the shaft 10 may be provided with a joint and forceps at its leading end in the positive direction of the Z-axis. The joint and the forceps correspond to movable parts.

The joint may be configured to allow changes in orientations of the forceps using the driving force transmitted from the sliders 40 (described below). A specific configuration of the joint may be a general configuration that allows changes in orientations of forceps using a driving force transmitted, and is not particularly limited to any specific configuration.

The forceps may have a configuration similar to general forceps for treatment of a patient. In some embodiments, a case in which the forceps are arranged at the leading end of the shaft 10 is described, but other instruments to be used for treatment of a patient may be arranged at the leading end of the shaft 10.

The casing 20 may include a first casing 20A and a second casing 20B. The first casing 20A and the second casing 20B are members forming an outer shape of the casing 20. The casing 20 may include a first end and a second end. The first end of the casing 20 is the end on a positive side in the Z-direction. The second end of the casing 20 may be opposite from the first end of the casing 20 in the end on a negative side in the Z-direction.

Figure 3:
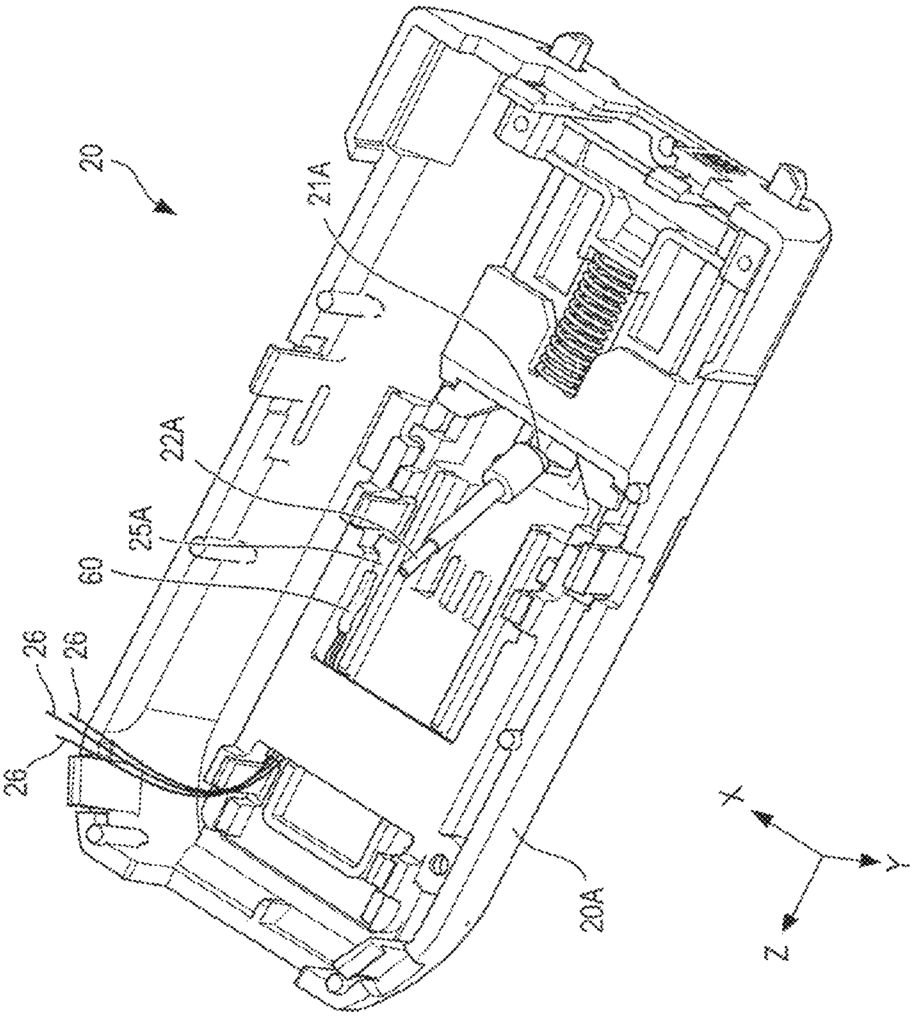
FIG. 3 is a perspective view of a first casing according to some embodiments.

As shown in FIGS. 1 and 3, the first casing 20A of the casing 20 is a member forming side faces and a top face of the casing 20, the faces being portions of the casing 20 on a positive side in the Y-axis direction. The first casing 20A may include a conductor 21A. The conductor 21A may be a member that is arranged on the top face of the first casing 20A and may conduct externally-supplied high-frequency current to the forceps.

The conductor 21A may be made of a conductive material, such as a metal material. The conductor 21A of some embodiments may be made of copper or an alloy containing copper as an ingredient. The conductor 21A may be arranged through the first casing 20A and may be electrically connected inside the casing 20 to a conductive wire 22A that conducts the high-frequency current to the forceps.

Figure 4:
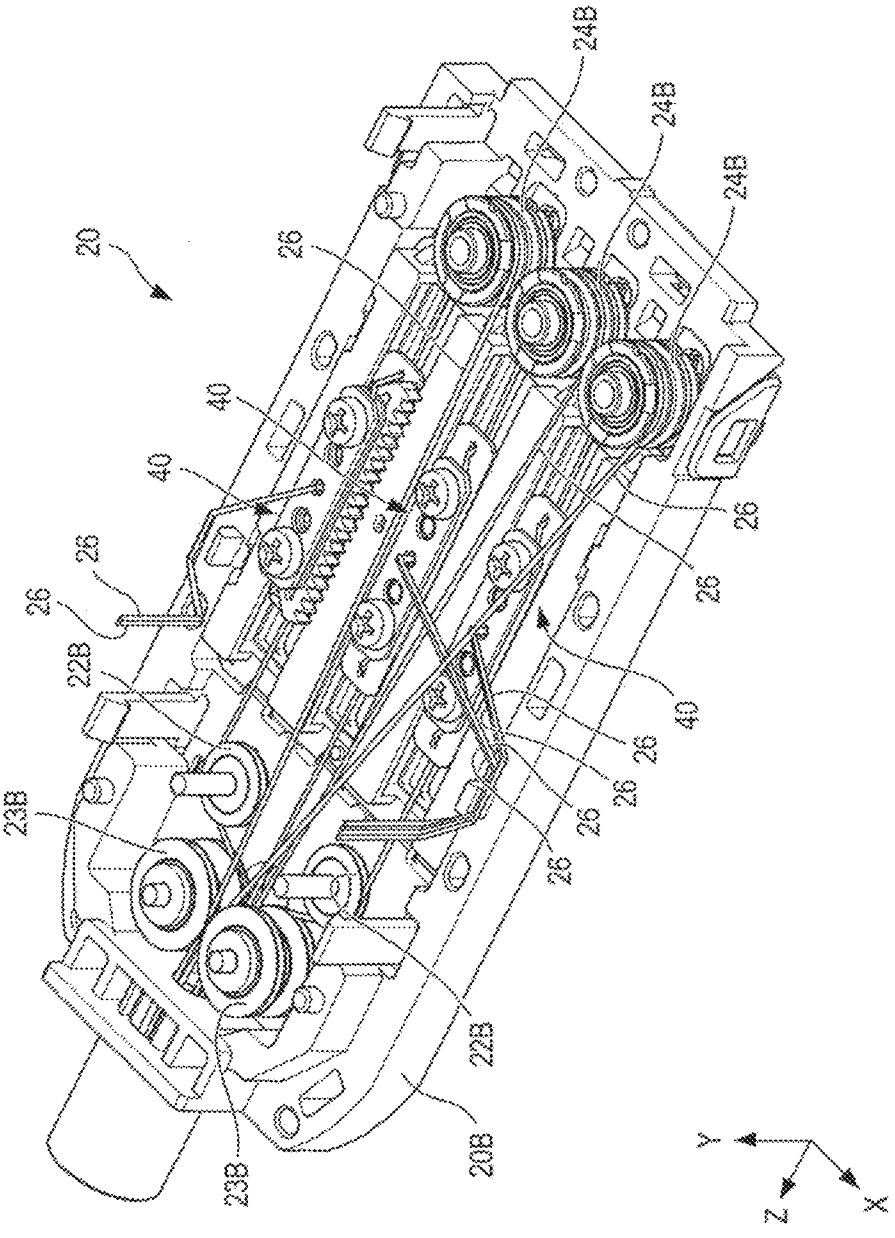
FIG. 4 is a perspective view of a second casing, wires, and sliders according to some embodiments.
Figure 5:
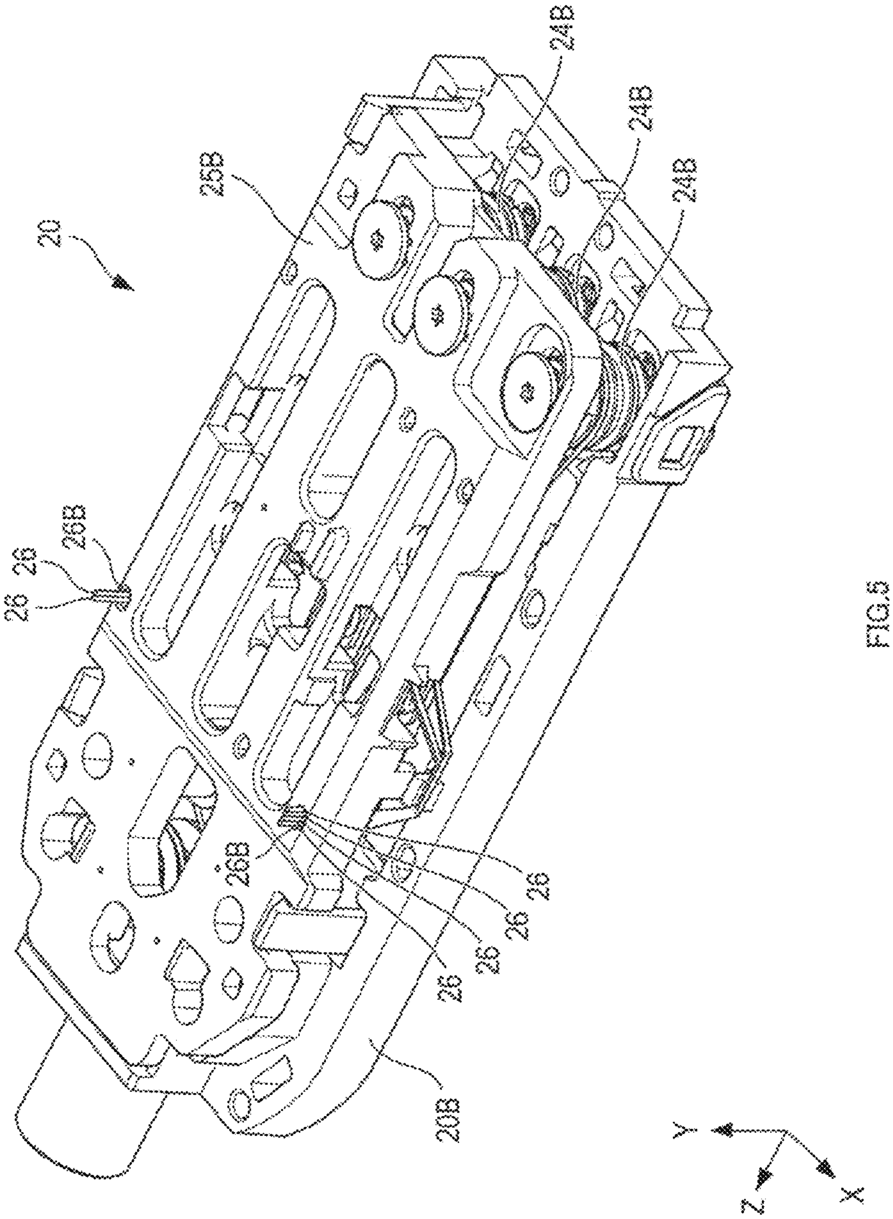
FIG. 5 is a perspective view of the second casing and the wires according to some embodiments.

As shown in FIGS. 1 and 2, the second casing 20B may be a plate-shaped member forming a bottom face of the casing 20 on a negative side in the Y-axis direction. As shown in FIG. 2, the second casing 20B may be provided with three driven grooves 21B and three sliders 40. Further, as shown in FIG. 4, the second casing 20B may be provided with three wires 26. Furthermore, as shown in FIG. 5, the second casing 20B may be provided with a cover 25B.

As shown in FIG. 2, the driven grooves 21B may be elongated holes provided in an end face of the second casing 20B located on a negative side in the Y-axis direction. In other words, the driven grooves 21B may be elongated holes provided on an attachment/detachment face where the second housing 20B and the multi-degree-of-freedom manipulator are attached/detached. Further, the driven grooves 21B may be configured to extend along the Z-axis.

The three driven grooves 21B may be arranged side by side at equal intervals in the X-axis direction. The number of the driven grooves 21B may be determined based on motions or the like of the joint, the forceps and/or the like. In other words, the number of the driven grooves 21B may be determined based on motions in accordance with a specification for the multi-degree-of-freedom manipulator. The number of the driven grooves 21B may be more than three or less than three.

The sliders 40 may be configured to receive the driving force from the multi-degree-of-freedom manipulator, and then transmit the driving force to the joint and/or forceps. The sliders 40 may be configured to be attachable to and detachable from the multi-degree-of-freedom manipulator.

The sliders 40 may be arranged to be relatively movable with respect to the casing 20. According to some embodiments, a case in which the sliders 40 are arranged may be relatively movable in a linear manner with respect to the casing 20. The sliders 40 may be arranged to be relatively rotatable with respect to the casing 20.

One slider 40 may be arranged on each of the three driven grooves 21B so as to be movable within the driven groove 21B in the Z-axis direction. In other words, the sliders 40 may be arranged so as to be relatively movable in a linear manner with respect to the casing 20. The slider 40 may be arranged on each of all driven grooves 21B, or on only some of the driven grooves 21B.

Some of the three sliders 40 may be configured to transmit the driving force to the forceps. The rest of the sliders 40 may be configured to transmit the driving force to the joint. According to some embodiments, two of the three sliders 40 may be configured to transmit the driving force to the forceps. Out of the three sliders 40, one slider 40, other than the sliders 40 transmitting the driving force to the forceps, may be configured to transmit the driving force to the joint.

Figure 9:
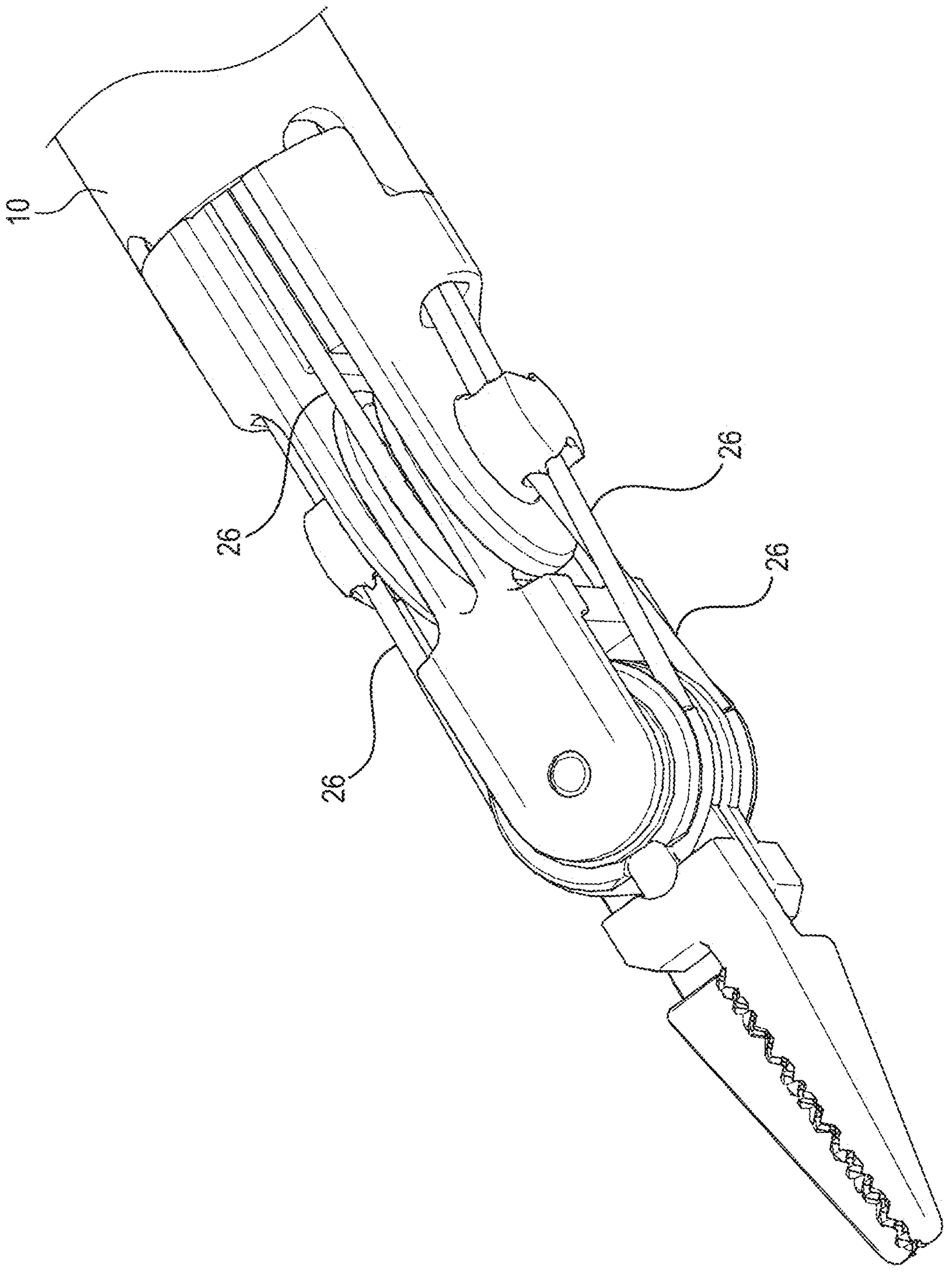
FIG. 9 is a perspective view of the wires and the moveable part according to some embodiments.

The wires 26 shown in FIG. 4 and FIG. 9 may be configured to transmit the driving force from the sliders 40 to the forceps or the joint. One slider may be provided with one or two wires 26.

The wires 26 may each be formed in a long shape using a conductive material. According to some embodiments, a case is described in which the wires 26 are made of metal materials such as stainless steel, tungsten, an alloy containing tungsten as an ingredient, and a piano wire, which are used in manipulators in surgical robot systems.

The cover 25B shown in FIG. 5 may be a plate-shaped member mounted on the second casing 20B and may be arranged on the positive side in the Y-axis direction with respect to the sliders 40. The cover 25B may include wire holes 26B through which the wires 26 are inserted.

Figure 6:
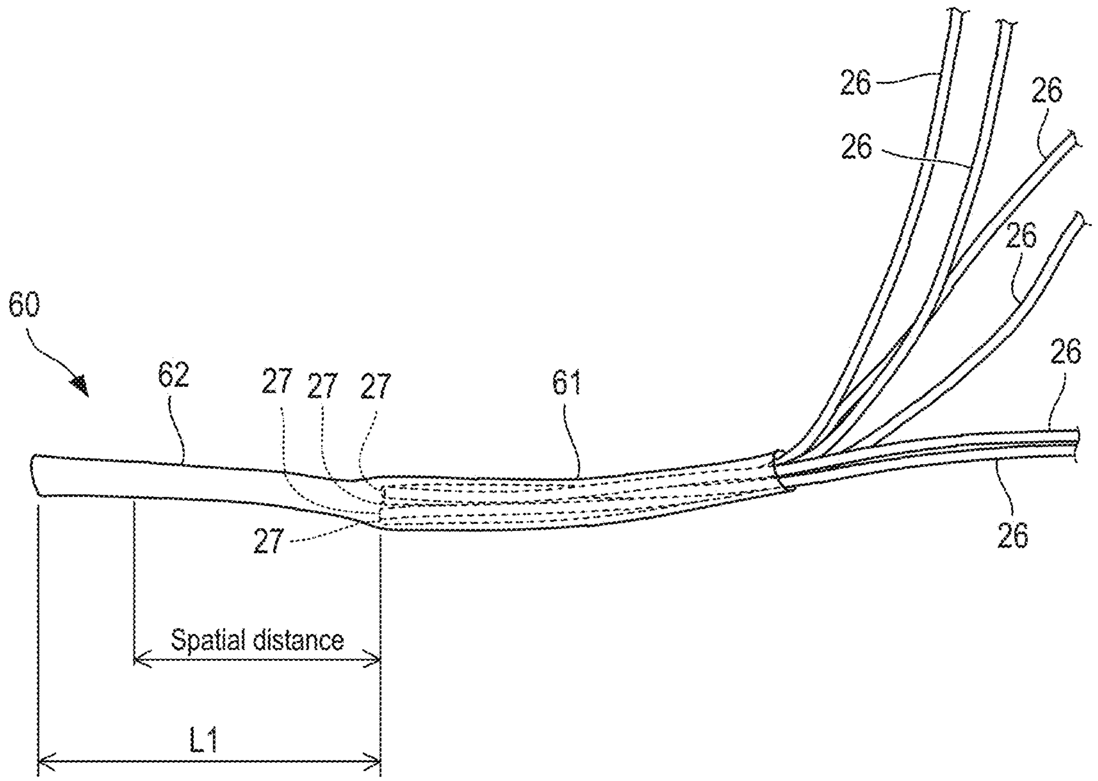
FIG. 6 is a partial enlarged view of an insulator according to some embodiments.

As shown in FIG. 6, an insulator 60 may be provided on end portions 27 of the wires 26 that extend from the sliders 40 to a side other than that of the forceps or the joint. More specifically, the insulator 60 may be provided on the end portions 27 of the wires 26 that are inserted through a later-described insertion hole 46 of the slider 40.

As shown in FIG. 5, the wires 26 may be inserted through the wire holes 26B of the cover 25B from the slider 40. The insulator 60 may be arranged on the end portions 27 of the wires 26 guided from the wire holes 26B to the positive-side in the Y-axis direction.

The insulator 60 may be a member covering a circumference of a plurality of end portions 27 of a plurality of wires 26. According to some embodiments, one insulator 60 may cover the end portions 27 of all the wires 26. However, one insulator 60 may cover an end portion 27 of one wire 26.

The insulator 60 may be a tubular member made of an insulating material. According to some embodiments, the insulator 60 may be made of an insulating resin material. The insulator 60 may be made of a resin material that will shrink when heat is applied.

Figure 10:
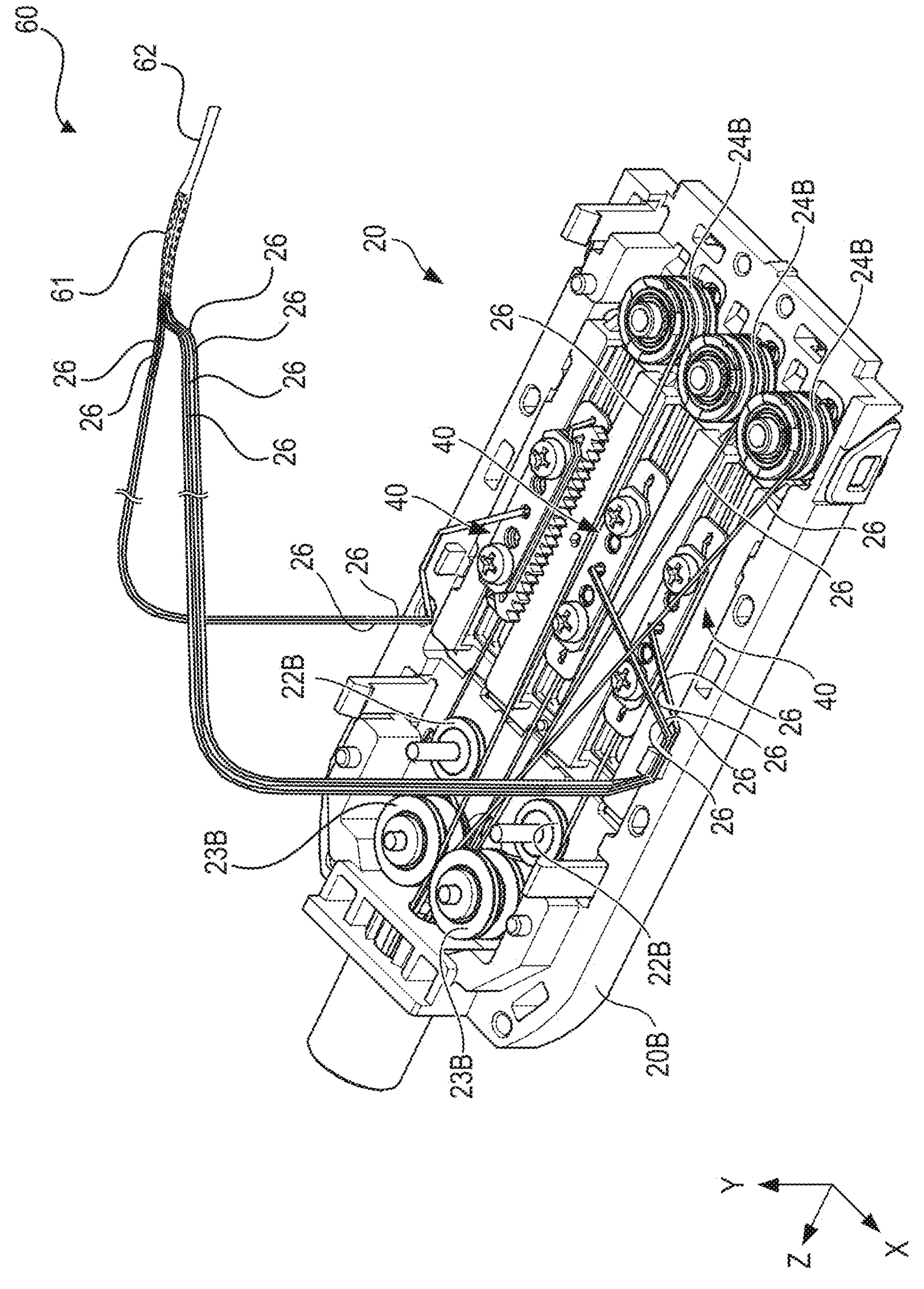
FIG. 10 is a perspective view of the surgical instrument according to some embodiments.

As shown in FIG. 6 and FIG. 10, the insulator 60 may include a covering area 61 and a non-covering area 62 that are continuously arranged in a longitudinal direction of the insulator 60. The covering area 61 may be an area where the wires 26 are arranged inside the insulator 60 in an inner part of a coaxial-section that intersects with the longitudinal direction of the insulator 60, in other words, inside a tubular shape. The non-covering area 62 may be an area where the wires 26 are not arranged inside the insulator 60.

The non-covering area 62 may have a specified length L1. The specified length L1 may be a length greater than or equal to a distance to ensure electrical insulation, which may be determined based on voltage of the high-frequency current supplied to the conductor 21A. The distance for ensuring electrical insulation may include a spatial distance.

A numerical value of the specified length L1 may be in the range of 3 mm or more and 80 mm or less. A numerical value of the specified length L1 may be in the range of 3 mm or more and 40 mm or less. According to the voltage of the high-frequency current supplied to the conductor 21A or the like, the numerical value of the specified length L1 may be selected from the aforementioned range.

The high-frequency current supplied to the conductor 21A is used for electrocautery during surgery. By setting the numerical value of the specified length L1 to 3 mm or more, a minimum spatial distance can be secured. By setting the numerical value of the specified length L1 to 80 mm or less, it is easier to inhibit reduction of workability to combine the first casing 20A and the second casing 20B to each other, and by setting the numerical value of the specified length L1 to 40 mm or less, it is much easier to inhibit reduction of workability to combine the first casing 20A and the second casing 20B to each other.

If the specified length L1 becomes longer, it is more difficult to arrange the wires 26 and the insulator 60 in a placement portion 25A, and the wires 26 may likely get caught between the first casing 20A and the second casing 20B. Accordingly, it is advantageous to work with care to ensure that wires do not get caught, which will be liable to reduction of workability.

As shown in FIG. 3, the wires 26 may have end portions 27 that may be inserted into the groove-shaped placement portion 25A from the positive side of the Z-axis direction to a negative side of the Z-axis direction. The groove-shaped placement portion 25A may be arranged on an inner surface of the first casing 20A. In FIG. 3, to make the figure easier to see, only three of six wires 26 are shown. The placement portion 25A may be a portion formed to extend in the Z-axis directions. The conductor 21A may be provided at a position adjacent to the placement portion 25 on the negative side in the Z-axis direction in the first casing 20A.

As shown in FIG. 4 and FIG. 10, two first guide pulleys 22B that guide the wires 26 to the shaft 10, two second guide pulleys 23B, and three third guide pulleys 24B may be provided within the second casing 20B of the casing 20.

The first guide pulleys 22B may be arranged closer to the shaft 10 than the sliders 40 are. The two first guide pulleys 22B may be arranged side by side, one of which is on a positive side in the X-axis direction, and the other is on a negative side in the X-axis direction.

The two first guide pulleys 22B may each guide, to the two second guide pulleys 23B, the wire 26 extending from the slider 40 located on the positive side in the X-axis direction and the wire 26 extending from the slider 40 located on the negative side in the X-axis direction.

The second guide pulleys 23B may be arranged closer to the shaft 10 than the sliders 40 are, similarly to the first guide pulley 22B. The two second guide pulleys 23B may be arranged side by side, one of which is on the positive side in the X-axis direction, and the other is on the negative side in the X-axis direction.

The two second guide pulleys 23B may guide, to an inside of the shaft 10, the wire 26 extending from the first guide pulley 22B located on the positive side in the X-axis direction and the wire 26 extending from the first guide pulley 22B located on the negative side in the X-axis direction.

The third guide pulleys 24B may be arranged more away from the shaft 10 than the sliders 40 are. The three third guide pulleys 24B may be arranged side by side in the X-axis direction. Each of the third guide pulleys 24B is formed in a cylindrical shape and may include two or more grooves on its cylindrical surface so as to guide the corresponding wire 26.

According to some embodiments, a case is described in which three grooves are provided at different positions in the Y-axis direction on the cylindrical surfaces of each third guide pulley 24B. Each of the three third guide pulleys 24B may be configured to allow the wire 26 to move from one groove that guides the wire 26 to a groove adjacent thereto.

Out of the three third guide pulleys 24B, the third guide pulley 24B on the negative side in the X-axis direction may cause the wire 26 extending from the slider 40 located on the negative side in the X-axis direction to move from the groove that is first guiding the wire 26 to an adjacent groove, so that the wire 26 is differently positioned in the Y-axis direction and then guided to the second guide pulley 23B located on the negative side in the X-axis direction. The second guide pulley 23B on the negative side in the X-axis direction may guide such wire 26 to the inside of the shaft 10.

The third guide pulley 24B in the center may cause the wire 26 extending from the slider 40 in the center to move from the groove that is first guiding the wire 26 to an adjacent groove, so that the wire 26 is differently positioned in the Y-axis direction and then guided to the second guide pulley 23B located on the positive side in the X-axis direction. The second guide pulley 23B on the positive side in the X-axis direction may guide the wire 26 to the inside of the shaft 10.

The third guide pulley 24B on the positive side in the X-axis direction may cause the wire 26 extending from the slider 40 located on the positive side in the X-axis direction to move from the groove that is first guiding the wire 26 to an adjacent groove, so that the wire 26 is differently positioned in the Y-axis direction and then guided to the second guide pulley 23B located on the positive side in the X-axis direction. The second guide pulley 23B on the positive side in the X-axis direction guides the wire 26 to the inside of the shaft 10.

Figure 7:
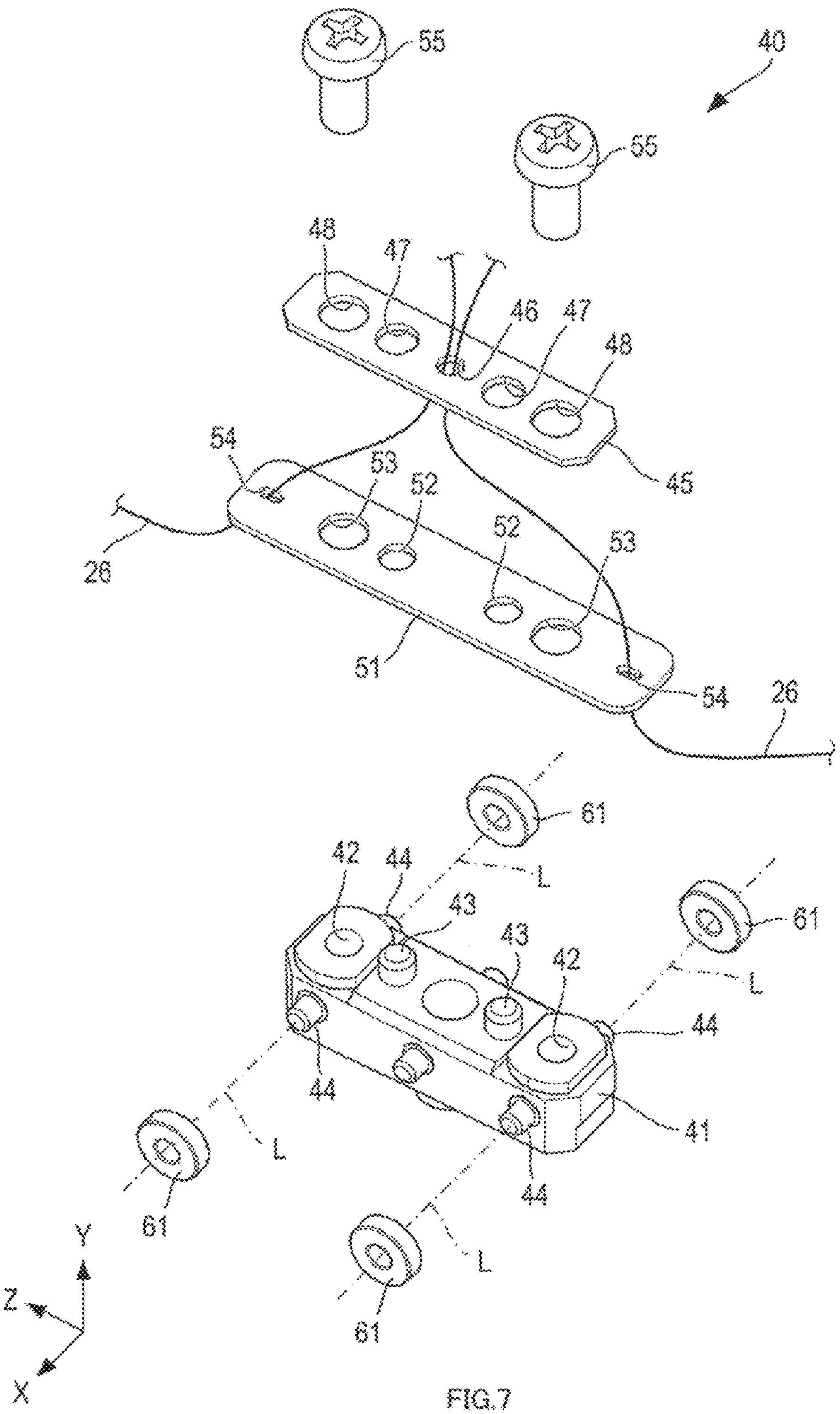
FIG. 7 is a perspective view of the wires and a slider according to some embodiments.
Figure 8:
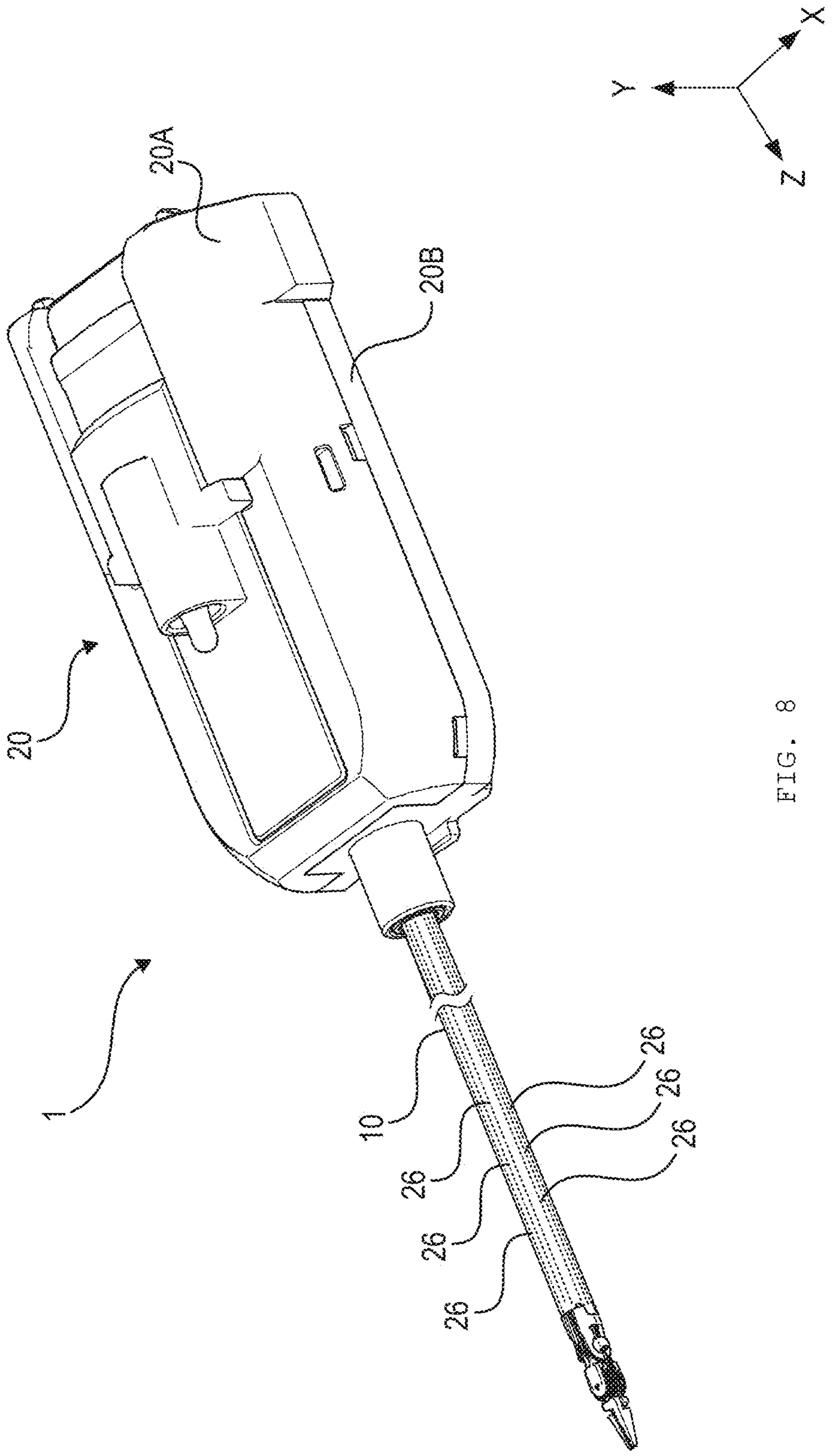
FIG. 8 is a perspective view of the surgical instrument according to some embodiments.

As shown in FIG. 7, the slider 40 may be provided with a slider body 41, one first clamping portion 45, one second clamping portion 51, two fixing members 55, and four rolling members 61. The slider 40 may comprise an additional member.

The slider body 41 may be a member formed in a pillar shape extending in the Z-axis direction. More specifically, the slider body 41 may be a member formed in a square column shape. The slider body 41 is provided with two female screw holes 42, two positioning protrusions 43, and four rolling shafts 44.

The female screw holes 42 match male screws (described below) of the fixing members 55. The female screw holes 42 may be screw holes used to hold the first clamping portion 45 and the second clamping portion 51. The two female screw holes 42 may be screw holes formed to extend in the Y-axis direction, one of which may be at an end part of the slider body 41 in the positive direction of the Z-axis, and the other of which may be at an end part of the slider body 41 in the negative direction of the Z-axis.

The positioning protrusions 43 may be protrusions that determine relative positions between the first clamping portion 45 and the second clamping portion 51 with respect to the slider body 41. The positioning protrusions 43 may be members each having a cylindrical shape and protruding from the slider body 41 in the positive direction of the Y-axis. The two positioning protrusions 43 may be provided at respective positions adjacent to the two female screw holes 42 and on a center part of the slider body 41 with respect to the two female screw holes 42.

The rolling shafts 44 may be members that support the rolling members 61 in a rotatable manner about rotation axes L. The rolling shafts 44 may be members each having a cylindrical shape and protruding from the slider body 41 in the X-axis direction. The center axis of each cylindrical shape may be an axis parallel to the X-axis and is a corresponding one of the rotation axes L.

The four rolling shafts 44 may be provided on the slider body 41, two of which are located in the end part in the positive Z-axis direction on a side face of the slider body 41 in the positive X-axis direction and a side face thereof in the negative X-axis direction, and the other two of which are located in the end part in the negative Z-axis direction on the side face of the slider body 41 in the positive X-axis direction and the side face thereof in the negative X-axis direction.

The first clamping portion 45 and the second clamping portion 51 may be members that hold the wire 26 therebetween. The first clamping portion 45 and the second clamping portion 51 may be overlapped and arranged on or above a surface of the slider body 41 located on a positive side in the Y-axis direction. The first clamping portion 45 may be arranged on the second clamping portion 51 on the positive side in the Y-axis direction. In other words, the second clamping portion 51 may be arranged on the first clamping portion 45 on the negative side in the Y-axis direction.

The first clamping portion 45 may have a rectangular plate-like shape elongated in the Z-axis direction. The first clamping portion 45 may include one insertion hole 46, two first positioning holes 47, and two first fixing holes 48.

The insertion hole 46 may be a through-hole through which an end of the wire 26 is inserted, and may have a smaller diameter than the first positioning holes 47 and the first fixing holes 48. According to some embodiments, the insertion hole 46 may be located in a central area of the first clamping portion 45 in the Z-axis direction. According to one or more embodiments, only the end portion of the wires 26 are covered by the insulator 60 such that the portion of the wires 26 that are positioned in the insertion hole 46 are not covered by the insulator 60. In other words, the end portion of the wires 26 that are covered by the insulator 60 are outside of the slider 40.

The first positioning holes 47 may be through-holes which are each formed to have an inner diameter larger than an outer diameter of each of the positioning protrusions 43 and through which the positioning protrusions 43 are inserted. In an attached state, the two first positioning holes 47 may be formed in respective positions on the first clamping portion 45 that are opposite to the positioning protrusions 43. According to some embodiments, the two first positioning holes 47 may be located in respective positions adjacent to the insertion hole 46, in other words, an adjacent position in the positive Z-axis direction and an adjacent position in the negative Z-axis direction.

The first fixing holes 48 may be through-holes which are each formed to have an inner diameter larger than an outer diameter of each male screw of the fixing members 55 and through which the fixing members 55 are inserted. In the attached state, the first fixing holes 48 may be formed in respective positions opposite to the female screw holes 42.

The two first fixing holes 48 may be formed in respective positions on the first clamping portion 45 such that the two first positioning holes 47 are arranged between the first fixing holes 48. According to some embodiments, one of the two first fixing holes 48 may be adjacent in the positive Z-axis direction to the first positioning hole 47 located on a positive side in the Z-axis direction, and the other of the two first fixing holes 48 may be adjacent in the negative Z-axis direction to the first positioning hole 47 located on the negative side in the Z-axis direction.

The second clamping portion 51 may be configured to have a rectangular plate-like shape elongated in the Z-axis direction. The second clamping portion 51 may be configured to have a longer dimension in the Z-axis direction than the first clamping portion 45. The second clamping portion 51 may include two second positioning holes 52, two second fixing holes 53, and two guide holes 54.

The second positioning holes 52 may be through-holes which are each formed to have an inner diameter larger than the outer diameter of each of the positioning protrusions 43 and through which the positioning protrusions 43 are inserted. The inner diameter of each second positioning hole 52 may be the same as or different from the inner diameter of each first positioning hole 47. In the attached state, the two second positioning holes 52 may be formed in respective positions on the second clamping portion 51 that are opposite to the positioning protrusions 43.

The second fixing holes 53 may be through-holes which are each formed to have an inner diameter larger than the outer diameter of each male screw of the fixing members 55 and through which the fixing members 55 may be inserted. The inner diameter of each second fixing hole 53 may be the same as or different from the inner diameter of each first fixing hole 48.

In the attached state, the two second fixing holes 53 may be formed in respective positions opposite to the female screw holes 42. The two second fixing holes 53 may be formed on the second clamping portion 51 such that the two second positioning holes 52 are located between the two second fixing holes 53.

According to some embodiments, one of the two second fixing holes 53 may be adjacent in the positive Z-axis direction to the second positioning hole 52 located on the positive side in the Z-axis direction, and the other of the two second fixing holes 53 may be adjacent in the negative Z-axis direction to the second positioning hole 52 located on the negative side in the Z-axis direction.

The guide holes 54 may be through-holes through which the wire 26 is inserted and are elongated holes extending in the Z-axis direction. The two guide holes 54 may be formed on the second clamping portion 51 such that the two second fixing holes 53 are located between the two guide holes 54.

According to some embodiments, the two guide holes 54 may be located in respective positions, one of which is adjacent in the positive Z-axis direction to the second fixing holes 53 located on the positive side in the Z-axis direction, and the other of which is adjacent in the negative Z-axis direction to the second fixing holes 53 located on the negative side in the Z-axis direction.

The positions where the two guide holes 54 are provided may be contained in an area where the second clamping portion 51 protrudes more than the first clamping portion 45 in the positive Z-axis direction and an area where the second clamping portion 51 protrudes more than the first clamping portion 45 in the negative Z-axis direction, in a state in which the first clamping portion 45 and the second clamping portion 51 are attached to the slider body 41.

The fixing members 55 may be configured to fix the first clamping portion 45 and the second clamping portion 51 in such a manner that the first clamping portion 45 and the second clamping portion 51 are arranged on or above the slider body 41. In addition, the fixing members 55 may be configured to fix the first clamping portion 45 and the second clamping portion 51 with the wire 26 being interposed therebetween. According to some embodiments, the fixing members 55 may be configured to include male screws.

The rolling members 61 may be supported by the rolling shafts 44 in a rotatable manner about the respective rotation axes L. The rolling members 61 may each be formed in a cylindrical or columnar shape and configured to have a hole in a center through which the corresponding rolling shaft 44 is inserted.

The four rolling members 61 may be arranged on the slider body 41, two of which may be located in the end part in the positive Z-axis direction on the side face of the slider body 41 in the positive X-axis direction and the side face thereof in the negative X-axis direction, and the other two of which may be located in the end part in the negative Z-axis direction on the side face of the slider body 41 in the positive X-axis direction and the side face thereof in the negative X-axis direction.

Next, an insulation between the end portions 27 of the wires 26 and the conductor 21A in the surgical instrument 1 with the aforementioned configurations is described below.

As shown in FIG. 4 and FIG. 10, when the sliders 40 move relatively along the driven grooves 21B, the wires 26 fixed to the sliders 40 may be pulled or pushed as the sliders 40 move. As the wires 26 are pulled or pushed, positions of the end portions 27 of the wires 26 may be changed.

More specifically, as shown in FIG. 3, the end portions 27 of the wires 26 move along the placement portion 25A, approaching or going away from the conductor 21A. Even when the end portions 27 of the wires 26 approach the conductor 21A, the specified length L1 between the end portions 27 of the wires 26 and the conductor 21A may be maintained. The non-covering area 62 may always be present and interposed between the end portions 27 of the wires 26 and the conductor 21A, such that the end portions 27 and the conductor 21A cannot be closer than a distance L1. This allows to maintain the insulation between the end portions 27 of the wires 26 and the conductor 21A.

According to the surgical instrument 1 of some embodiments, the end portions 27 of the wires 26 may be covered by the insulator 60. The insulator 60 may include the non-covering area 62 with none of the wires 26 arranged inside the insulator 60, so that it is easier to maintain the insulation without increasing a distance between the end portions 27 of the wires 26 and the conductor 21A.

More specifically, it is possible to reduce a size of the casing 20 inside which the wires 26 and the conductor 21A are housed, and to set a smaller distance between ports in robotic endoscopic surgery. As a result, it is possible to apply robotic surgery to various surgical procedures.

The non-covering area 62 of the insulator 60 has the specific length L1 greater than or equal to the spatial distance, so that it is easier to maintain the insulation between the end portions 27 of the wires 26 and the conductor 21A.

The plurality of end portions 27 of the plurality of wires 26 may be brought together and covered by the insulator 60. By covering the plurality of end portions 27 of the plurality of wires 26 with the insulator 60 together, it is easier to maintain the insulation between such plurality of end portions 27 and the conductor 21A.

While various embodiments have been described above with reference to the drawings, the present disclosure is not limited thereto, and any combination or substitution of components as appropriate is included within the scope of the present disclosure. In some embodiments, modifications such as combinations, changes in the order of processes, and various changes in design may be made on the basis of knowledge of a person skilled in the art, and such modified embodiments are within the scope of the present disclosure and the appended claims.

What is claimed is:

1. A surgical instrument comprising:

a casing comprising a first end and a second end, the second end being opposite from the first end;

a moveable part attached to a shaft extending from the first end of the casing;

at least one slider movable with respect to the casing;

at least one wire being held by the at least one slider, the at least one wire being configured to transmit movement from the at least one slider to the movable part;

a conductor arranged in the casing and configured to conduct electric power to the movable part; and an insulator that covers an end portion of the at least one wire that extends from the at least one slider toward the second end of the casing, wherein the insulator comprises:

a first portion covering the end portion of the at least one wire; and a second portion extending from an end of the end portion of the at least one wire and not covering the at least one wire.

2. The surgical instrument according to claim 1, wherein the at least one slider is linearly movable with respect to the casing.

3. The surgical instrument according to claim 1, wherein the second portion of the insulator has a length greater than or equal to a spatial distance, and wherein the spatial distance is based on the electric power to be supplied to the conductor.

4. The surgical instrument of claim 3, wherein the length of the second portion of the insulator is 3 mm to 80 mm.

5. The surgical instrument of claim 3, wherein the length of the second portion of the insulator is 3 mm to 40 mm.

6. The surgical instrument according to claim 1, wherein the at least one wire comprises a plurality of wires, and wherein the insulator covers the end portions of the plurality of wires.

7. The surgical instrument of claim 1, wherein the at least one wire is made of at least one of stainless steel, tungsten, an alloy containing tungsten, or a piano wire.

8. The surgical instrument of claim 1, wherein the insulator is tubular.

9. The surgical instrument of claim 1, wherein the first portion and the second portion are continuously arranged in a longitudinal direction of the insulator.

10. The surgical instrument of claim 1, wherein the first portion is a portion of the insulator in which the at least one wire is arranged inside in an inner part of a coaxial-section intersecting a longitudinal direction of the insulator.

11. The surgical instrument of claim 1, wherein the second portion is a portion of the insulator in which the at least one wire is not arranged inside.

12. The surgical instrument of claim 1, wherein the movable part is a joint and a forceps.

13. The surgical instrument of claim 12, wherein the at least one wire is configured to move the joint to change an orientation of the forceps based on a movement of the at least one slider.

14. The surgical instrument of claim 1, wherein the casing comprises a first casing and a second casing, and the first casing comprising the conductor.

15. The surgical instrument of claim 14, wherein the first casing forms a plurality of side faces and a top face of the casing, and wherein the conductor is arranged on the top face of the casing.

16. The surgical instrument of claim 14, wherein the second casing forms a bottom face of the casing, and wherein the second casing comprises the at least one slider and the at least one wire, the at least one slider being arranged in at least one groove on the second casing.

17. The surgical instrument of claim 1, wherein the conductor is made of copper or an alloy containing copper.

18. The surgical instrument of claim 1, wherein the at least one slider comprises a plurality of sliders, the at least one wire comprises a plurality of wires, and each slider is provided with one or two wires of the plurality of wires.

19. A surgical instrument comprising:

a casing comprising a first end and a second end, the second end being opposite from the first end;

a joint and a forceps attached to a shaft extending from the first end of the casing;

a plurality of sliders being linearly movable with respect to the casing;

a plurality of wires held by the plurality of sliders, an end portion of each of the plurality of wires extending from the plurality of sliders toward the second end of the casing, the plurality of wires being configured to transmit a driving force from the plurality of sliders to the joint and the forceps;

a conductor arranged in the casing and configured to conduct high-frequency current to the joint and the forceps; and an insulator covering an end portion of the plurality of wires that extends from the plurality of sliders toward the second end of the casing, wherein the insulator comprises:

a first portion covering the end portions of the plurality of wires; and a second portion extending from an end of the end portions of the plurality of wires and not covering the plurality of wires, the second portion having a length based on the high frequency current.

20. The surgical instrument according to claim 19, wherein the length of the second portion of the insulator is greater than or equal to a spatial distance based on the electric power to be supplied to the conductor, and wherein the end portion of the plurality of wires comprises a plurality of end portions and the insulator covers the plurality of end portions of the plurality of wires.

* * * * *